(12) United States Patent
Kernbaum et al.

(10) Patent No.: US 10,772,693 B2
(45) Date of Patent: Sep. 15, 2020

(54) SURGICAL INSTRUMENT SHAFT

(71) Applicant: INTUITIVE SURGICAL OPERATIONS, INC., Sunnyvale, CA (US)

(72) Inventors: Nicole Kernbaum, Sunnyvale, CA (US); Samuel T. Crews, Palomar Park, CA (US); Harsukhdeep Singh Ratia, Foster City, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 432 days.

(21) Appl. No.: 15/391,040

(22) Filed: Dec. 27, 2016

(65) Prior Publication Data

US 2017/0172677 A1    Jun. 22, 2017

Related U.S. Application Data

(63) Continuation of application No. 14/206,821, filed on Mar. 12, 2014, now abandoned.
(Continued)

(51) Int. Cl.
*A61B 34/35* (2016.01)
*A61B 34/37* (2016.01)
(Continued)

(52) U.S. Cl.
CPC .............. *A61B 34/35* (2016.02); *A61B 1/05* (2013.01); *A61B 17/2841* (2013.01);
(Continued)

(58) Field of Classification Search
CPC .... A61B 2017/2901; A61B 2017/2905; A61B 2017/2917; A61B 19/2203; A61B 2017/29011; A61B 17/1285; A61B 17/32011; A61B 10/02; A61B 17/320016; A61B 17/28; A61B 17/0483;
(Continued)

(56) References Cited

U.S. PATENT DOCUMENTS 4,616,631 A    10/1986  Takahashi
5,325,845 A *   7/1994  Adair ................... A61B 1/0055
                                                       600/114

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Robert A Lynch
(74) *Attorney, Agent, or Firm* — Jones Robb, PLLC

(57)    ABSTRACT

A surgical instrument may include a shaft, a force transmission mechanism, and an end effector. The shaft may have a proximal end and a distal end. The force transmission mechanism may be coupled to the proximal end of the shaft. The end effector may be coupled to the distal end of the shaft. The shaft may include a body having an outer surface and an inner surface. The inner surface may surround a lumen configured to receive a drive member that extends through the lumen. The outer surface of the body may form an outer surface of the shaft. The body may be made of a single material from the inner surface of the body to the outer surface of the body.

17 Claims, 11 Drawing Sheets

Related U.S. Application Data

(60) Provisional application No. 61/781,679, filed on Mar. 14, 2013.

(51) Int. Cl.
| | | |
|---|---|---|
| *A61B 34/30* | (2016.01) | |
| *B29C 48/09* | (2019.01) | |
| *B29C 48/21* | (2019.01) | |
| *A61B 34/00* | (2016.01) | |
| *A61B 1/05* | (2006.01) | |
| *A61B 17/28* | (2006.01) | |
| *A61B 17/29* | (2006.01) | |

(52) U.S. Cl.
CPC .............. *A61B 34/30* (2016.02); *A61B 34/37* (2016.02); *A61B 34/71* (2016.02); *B29C 48/09* (2019.02); *B29C 48/21* (2019.02); *A61B 2017/2901* (2013.01); *A61B 2217/007* (2013.01)

(58) Field of Classification Search
CPC ..... A61B 17/2211; A61B 17/44; A61B 17/29; A61B 17/29091; A61B 17/282; A61B 17/30; A61B 17/220311; A61B 17/320092; A61B 2034/3011; A61B 2034/302; A61B 2034/303; A61B 2034/305; A61B 34/35; A61B 34/711; A61B 2034/715; A61B 18/1442; A61B 18/1445; A61B 18/1447; A61B 17/22031; B29C 47/065; B29C 47/0023; B25B 7/00; A61M 2025/0031; A61M 2025/0036; A61M 2025/0039; A61M 2025/004; A61M 2025/0042; A61M 25/0026; A61M 25/0028; A61M 25/0029; A61M 25/003; A61M 25/0032; A61M 25/0041
See application file for complete search history.

(56) References Cited

U.S. PATENT DOCUMENTS

| | | | |
|---|---|---|---|
| 6,817,974 | B2 | 11/2004 | Cooper et al. |
| 8,545,515 | B2 | 10/2013 | Prisco et al. |
| 8,621,939 | B2 | 1/2014 | Blumenkranz et al. |
| 2001/0031975 | A1 | 10/2001 | Whitman et al. |
| 2002/0138082 | A1 | 9/2002 | Brock et al. |
| 2003/0036748 | A1* | 2/2003 | Cooper ............ A61B 17/00234 606/1 |
| 2003/0149338 | A1 | 8/2003 | Francois et al. |
| 2004/0138700 | A1* | 7/2004 | Cooper .................. A61B 1/008 606/205 |
| 2004/0167515 | A1 | 8/2004 | Petersen et al. |
| 2005/0273085 | A1* | 12/2005 | Hinman ................ A61B 1/0055 606/1 |
| 2007/0149971 | A1* | 6/2007 | Nishimura ......... A61B 18/1445 606/51 |
| 2007/0198011 | A1* | 8/2007 | Sugita ................ A61B 18/1492 606/46 |
| 2007/0221700 | A1 | 9/2007 | Ortiz et al. |
| 2007/0221701 | A1* | 9/2007 | Ortiz .................... A61B 17/068 227/175.1 |
| 2008/0046000 | A1 | 2/2008 | Lee et al. |
| 2008/0065105 | A1 | 3/2008 | Larkin et al. |
| 2008/0177283 | A1 | 7/2008 | Lee et al. |
| 2009/0157092 | A1 | 6/2009 | Blumenkranz et al. |
| 2009/0192522 | A1 | 7/2009 | Blumenkranz |
| 2009/0252926 | A1 | 10/2009 | Henderson et al. |
| 2010/0011901 | A1 | 1/2010 | Burbank |
| 2010/0042097 | A1* | 2/2010 | Newton ............. A61B 18/1445 606/41 |
| 2010/0160929 | A1* | 6/2010 | Rogers .................. A61B 17/29 606/130 |
| 2010/0168722 | A1 | 7/2010 | Lee et al. |
| 2010/0298843 | A1* | 11/2010 | Blumenkranz ........ A61B 34/30 606/130 |
| 2010/0313679 | A1 | 12/2010 | Larkin et al. |
| 2011/0071347 | A1 | 3/2011 | Rogers et al. |
| 2011/0071541 | A1 | 3/2011 | Prisco et al. |
| 2011/0071542 | A1* | 3/2011 | Prisco ............... A61M 25/0105 606/130 |
| 2011/0071543 | A1 | 3/2011 | Prisco et al. |
| 2011/0163146 | A1* | 7/2011 | Ortiz ............... A61B 17/07207 227/175.1 |
| 2011/0196419 | A1* | 8/2011 | Cooper ............. A61B 18/1445 606/206 |
| 2012/0277762 | A1 | 11/2012 | Lathrop et al. |
| 2013/0310814 | A1* | 11/2013 | Bacher .................. A61B 17/00 606/1 |
| 2014/0182733 | A1 | 7/2014 | Mettee, II et al. |
| 2015/0053293 | A1 | 2/2015 | Ophaug |
| 2015/0313619 | A1* | 11/2015 | Tadano .................. A61B 34/71 606/130 |
| 2015/0366573 | A1* | 12/2015 | Hahnle .................. A61B 17/29 606/205 |
| 2016/0143633 | A1* | 5/2016 | Robert .................. A61B 17/29 604/95.04 |

\* cited by examiner

SURGICAL INSTRUMENT SHAFT

This application is a continuation of U.S. patent application Ser. No. 14/206,821, filed on Mar. 12, 2014, which claims the benefit of U.S. Provisional Application No. 61/781,679, filed on Mar. 14, 2013, each of which is incorporated by reference herein in its entirety.

TECHNICAL FIELD

Aspects of the present disclosure relate to a surgical instrument, for example for use with a teleoperated (robotic) surgical system. In particular, aspects of the present disclosure relate to the shaft construction of such a surgical instrument.

INTRODUCTION

Some minimally invasive surgical techniques are performed remotely through the use of teleoperated (robotically-controlled) surgical instruments (which may also be referred to as tools). In teleoperated surgical systems, surgeons manipulate input devices at a surgeon console, and those inputs are passed to a patient side cart that interfaces with one or more teleoperated surgical instruments. Based on the surgeon's inputs at the surgeon console, the one or more surgical instruments are actuated at the patient side cart to operate on the patient, thereby creating a master-slave control relationship between the surgeon console and the surgical instrument(s) at the patient side cart.

Teleoperated surgical systems may have multiple arms to which teleoperated surgical instruments may be coupled. Because the surgical instruments may be used within a relatively small space inside of a patient during a surgical procedure, and because it is desirable to minimize the size of incisions and ports through which a surgical instrument may be passed to access the surgical site, and to otherwise minimize the invasiveness of a surgical procedure, components of a surgical instrument can be relatively small in size. Although components of a surgical instrument may be relatively small, it remains desirable that the components exhibit properties that allow them to perform various functions that may be required during a surgical procedure. To some degree, the issues of size and functionality may provide countervailing considerations when designing and manufacturing a surgical instrument. In view of these considerations, it may be desirable to provide a surgical instrument that has a robust design and provides mechanical properties that support the functions for which a surgical instrument may be used. It also may be desirable to provide such a surgical instrument that facilitates manufacture.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical instrument comprises a shaft, a force transmission mechanism, and an end effector. The shaft may have a proximal end and a distal end. The force transmission mechanism may be coupled to the proximal end of the shaft. The end effector may be coupled to the distal end of the shaft. The shaft may include a body having an outer surface and an inner surface. The inner surface may surround a lumen configured to receive a drive member that extends through the lumen. The outer surface of the body may form an outer surface of the shaft. The body may be made of a single material from the inner surface of the body to the outer surface of the body.

In accordance with at least one exemplary embodiment, a surgical instrument comprises a shaft, a force transmission mechanism, and an end effector. The shaft may have a proximal end and a distal end. The force transmission mechanism may be coupled to the proximal end of the shaft. The end effector may be coupled to the distal end of the shaft. The shaft may include a body having an outer surface that forms an outer surface of the shaft and an inner surface that defines a lumen that a drive member extends through. The body may have a single piece construction.

In accordance with at least one exemplary embodiment, a method of manufacturing a shaft for a surgical instrument comprises extruding a material to form a body of a shaft. The body may have an outer surface and an inner surface that forms a lumen configured to receive a drive member that extends through the lumen. The outer surface of the body may form an outer surface of the shaft. The body may be made of a single material from the inner surface of the body to the outer surface of the body.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
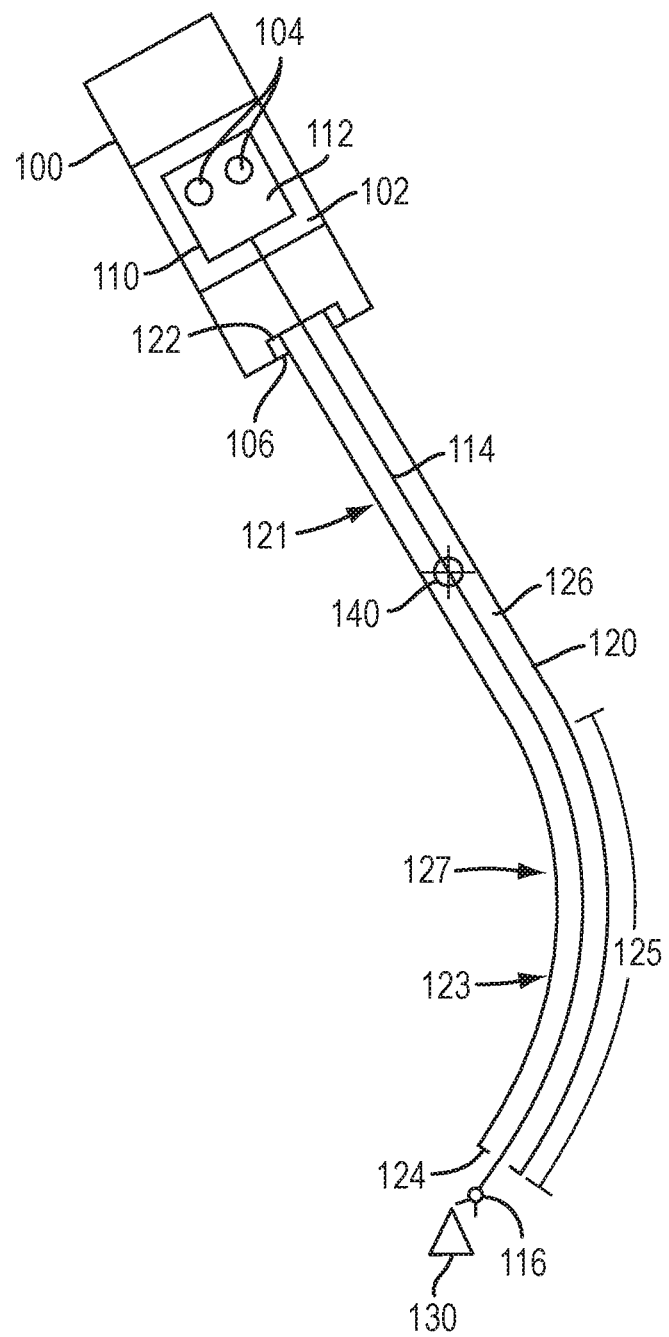
FIG. 1 is a schematic view of an exemplary embodiment of a portion of a manipulator supporting a curved cannula and a surgical instrument.

Exemplary embodiments discussed herein regard a surgical instrument for a teleoperated surgical system. The surgical instrument may facilitate manufacture, while providing a robust design with properties that support the functions for which the instrument is intended. In various exemplary embodiments, for example, a shaft of the surgical instrument may be configured to have a substantially uniform stiffness. Further, various exemplary embodiments enable substantial consistency in the manufacture of one shaft to the next.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Teleoperated surgery generally involves the use of a manipulator that has multiple manipulator arms. One or more of the manipulator arms often support a teleoperated surgical instrument that is ultimately placed in a master-slave relationship with master controllers at a surgeon console, such that inputs by a surgeon at the surgeon console are provided as signals to control movement of the surgical instruments. One or more of the manipulator arms typically also is used to support a surgical image capture device, such as a camera endoscope (which may be any of a variety of structures such as a laparoscope, an arthroscope, a hysteroscope, or the like), or, optionally, some other imaging modality (such as ultrasound, fluoroscopy, magnetic resonance imaging, or the like) so as to provide the surgeon with a view of the remote surgical site. Typically, at least three manipulator arms will respectively support two surgical tools (corresponding to the two hands of a surgeon) and an image capture device. Reference is made to U.S. application Ser. No. 12/618,583, entitled "Curved Cannula Surgical System," filed on Nov. 13, 2009 and published as U.S. Pub. No. US 2011/0071542 on Mar. 24, 2011, now issued as U.S. Pat. No. 8,545,515, which is hereby incorporated by reference in its entirety, for examples of a teleoperated surgical system.

Turning to FIG. 1, a schematic view of a portion of a patient side manipulator (or "PSM") that supports and moves a combination of a curved cannula and a passively flexible surgical instrument is shown, according to an exemplary embodiment. As depicted in FIG. 1, a surgical instrument 110 includes a force transmission mechanism 112, a flexible shaft 114, and an end effector 116. According to an exemplary embodiment, shaft 114 of instrument 110 may be passively flexible. Instrument 110 is mounted on an instrument carriage assembly 102 of manipulator 100. Interface discs 104 couple actuation forces from servo actuators in manipulator 100 to move instrument 110 components.

According to an exemplary embodiment, end effector 116 operates with a single degree of freedom (DOF) (e.g., closing jaws). According to an exemplary embodiment, instrument 110 may include a wrist structure (not shown) to provide one or more end effector DOF's (e.g., pitch, yaw; see e.g., U.S. Pat. No. 6,817,974 (filed Jun. 28, 2002) (disclosing "Surgical Tool Having Positively Positionable Tendon-Actuated Multi-Disk Wrist Joint"), which is incorporated herein by reference). An instrument 110, as shown in the exemplary embodiment of FIG. 1, lacking a wrist may be referred to as a non-wristed instrument. Omitting a wrist, for example, can simplify the number of actuation force interfaces between manipulator 100 and instrument 110; such omission can also reduce the number of force transmission elements (and hence, instrument complexity and dimensions) that would be utilized between the proximal force transmission mechanism 112 and the distally actuated end effector 116 in order to actuate a wrist structure.

FIG. 1 further shows a curved cannula 120, which has a proximal end 122, a distal end 124, and a central channel 126 that extends between proximal end 122 and distal end 124. According to an exemplary embodiment, curved cannula 120 is a rigid, single piece cannula. Curved cannula 120 may include one or more straight sections 121 and one or more curved sections 123, according to an exemplary embodiment. According to an exemplary embodiment, curved cannula 120 may be curved (not shown) from proximal end 122 to distal end 124. A curved section 125 of a curved cannula 120 may have a curvature with an angle between ends of section 125, for example, ranging from about 40° to about 65°. In another example, curved section 125 may have a curvature ranging from about 45° or about 60°. Curved section 123 may have a centerline radius 127, shown in the exemplary embodiment of FIG. 1, ranging from about 4.50 inches to about 5.50 inches, for example.

As depicted in the exemplary embodiment of FIG. 1, proximal end 122 of curved cannula 120 is mounted on a cannula mount 106 of manipulator 100. During use, flexible shaft 114 of instrument 110 extends through the central channel 126 of curved cannula 120 so that a distal portion of flexible shaft 114 and end effector 116 extend beyond distal end 124 of cannula 120 in order to reach a surgical site 130. Constraints of manipulator 100 (whether mechanical and/or preprogrammed software constraints in the control system for manipulator 100) cause instrument 110 and curved cannula 120 to move in pitch and yaw around remote center of motion 140 located along cannula 120, which may be located at an incision or port in a patient's body wall. The I/O actuation of manipulator 100, provided by carriage 102, inserts and withdraws instrument 110 through cannula 120 to move end effector 116 in and out.

Figure 2:
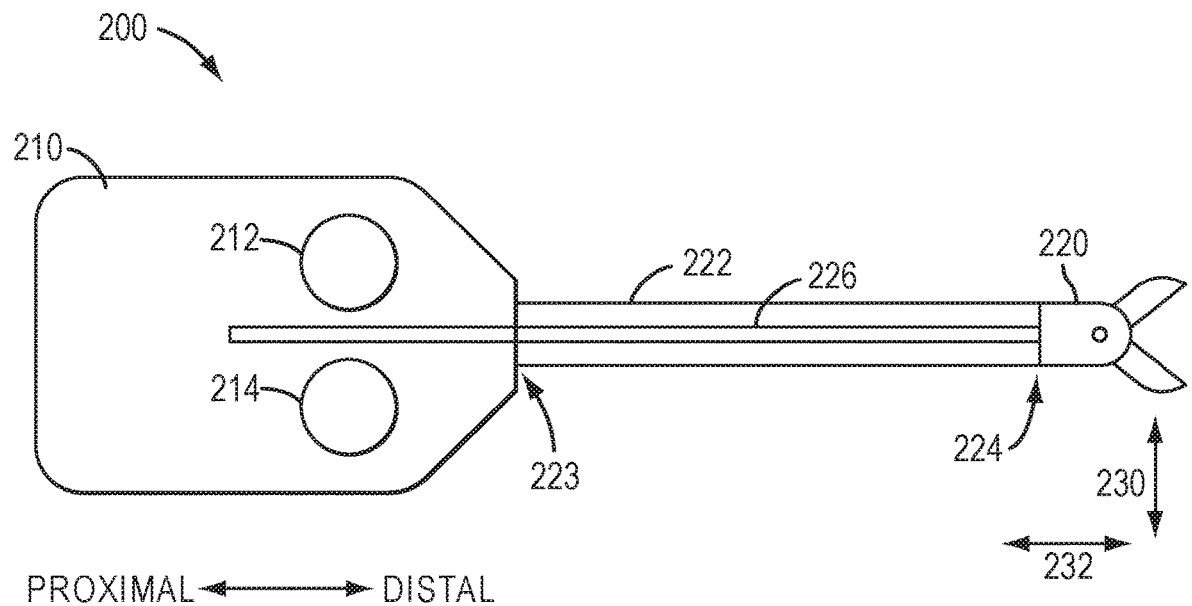
FIG. 2 is a top schematic view of an exemplary embodiment of a surgical instrument including a force transmission mechanism.

FIG. 2 depicts a top view of an exemplary embodiment of a surgical instrument 200 for a teleoperated surgical system. Surgical instrument 110 of FIG. 1 may be configured according to the exemplary embodiment of FIG. 2. Surgical instrument 200 may include a force transmission mechanism 210, a shaft 222 connected to force transmission mechanism 210 at a proximal end 223 of shaft 222, and an end effector 220 connected to a distal end 224 of shaft 222. Surgical instrument 200 may include one or more members to translate force between force transmission mechanism 210 and end effector 220. For instance, one or more drive member(s) 226 may connect force transmission mechanism 210 to end effector 220 to provide actuation forces to end effector 220, such as by extending through an interior of shaft 222.

By utilizing drive member(s) 226, force transmission mechanism 210 may actuate end effector 220, for example, to control a wrist structure (if any) of instrument 200 and/or to control a jaw of end effector 220 (or other moveable part). Further, because end effector 220 may be fixed to shaft 222, force translated from force translation mechanism 210 to end effector 220 may in turn be translated to shaft 222, such as when force translation mechanism 210 actuates end effector 220 and shaft 222 in a rolling motion. Drive member(s) 226 may be in the form of tension elements, such as when force transmission mechanism 210 is a pull-pull mechanism, as described in U.S. Pub. No. US 2011/0071542, or one or more drive element rods, such as when force transmission mechanism 210 is a push-pull mechanism, as described in U.S. Pub. No. US 2011/0071542.

Force transmission mechanism 210 may include one or more components to engage with a patient side cart of a teleoperated surgical system to translate a force provided by patient side cart to surgical instrument 200. According to an exemplary embodiment, force transmission mechanism 210 may include one or more interface disks 212, 214 that engage with a manipulator of a patient side cart, as discussed above in regard to the exemplary embodiment of FIG. 1. Thus, interface disks 212, 214 utilize actuation forces from a manipulator to actuate instrument 200. For instance, first disk 212 may be configured to provide a rolling motion to shaft 222 and provide a roll DOF for end effector 220, while second disk 214 may operate a jaw mechanism of end effector 220 to open and close. However, these particular actuation schemes/controls are exemplary only and other configurations are envisioned, depending on the type of instrument and motions for use of such instruments.

As discussed above, a shaft of a surgical instrument may be flexible. Flexibility, for example, may assist with inserting the instrument through a curved cannula. However, the instrument shaft may also be required to support an end effector when the distal end of the shaft and the end effector are extended beyond a distal end of the curved cannula. For instance, the shaft 114 of instrument 110 shown in the exemplary embodiment of FIG. 1 may be flexible to permit instrument 110 to be inserted and withdrawn through curved cannula 120 but also be sufficiently stiff to provide effective surgical action at a surgical site 130. As a result, flexible shaft 114 of instrument 110 may be extended through the central channel 126 of curved cannula 120 so that a distal portion of flexible shaft 114 and end effector 116 extend beyond the distal end 124 of cannula 120 to reach surgical site 130. In view of these considerations, a shaft of a surgical instrument may include structures to affect the flexibility and stiffness of the shaft.

Figure 3:
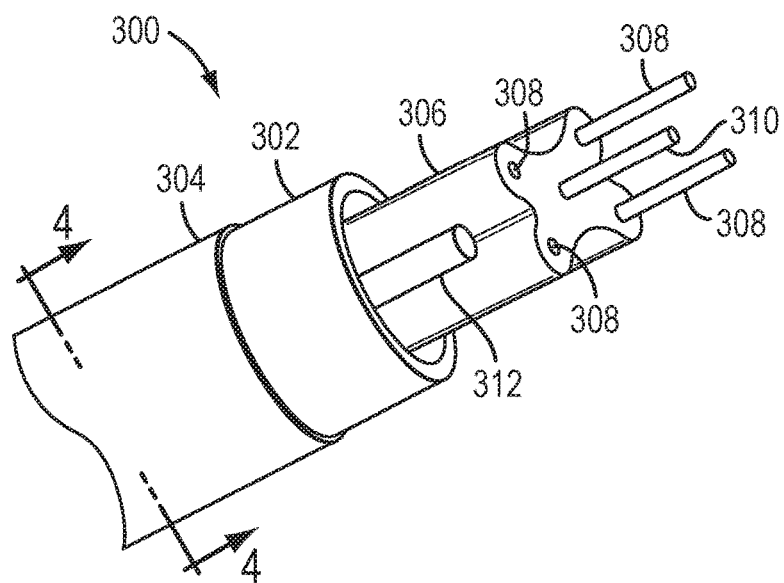
FIG. 3 is an exploded view of an exemplary embodiment of a shaft of a surgical instrument.
Figure 4:
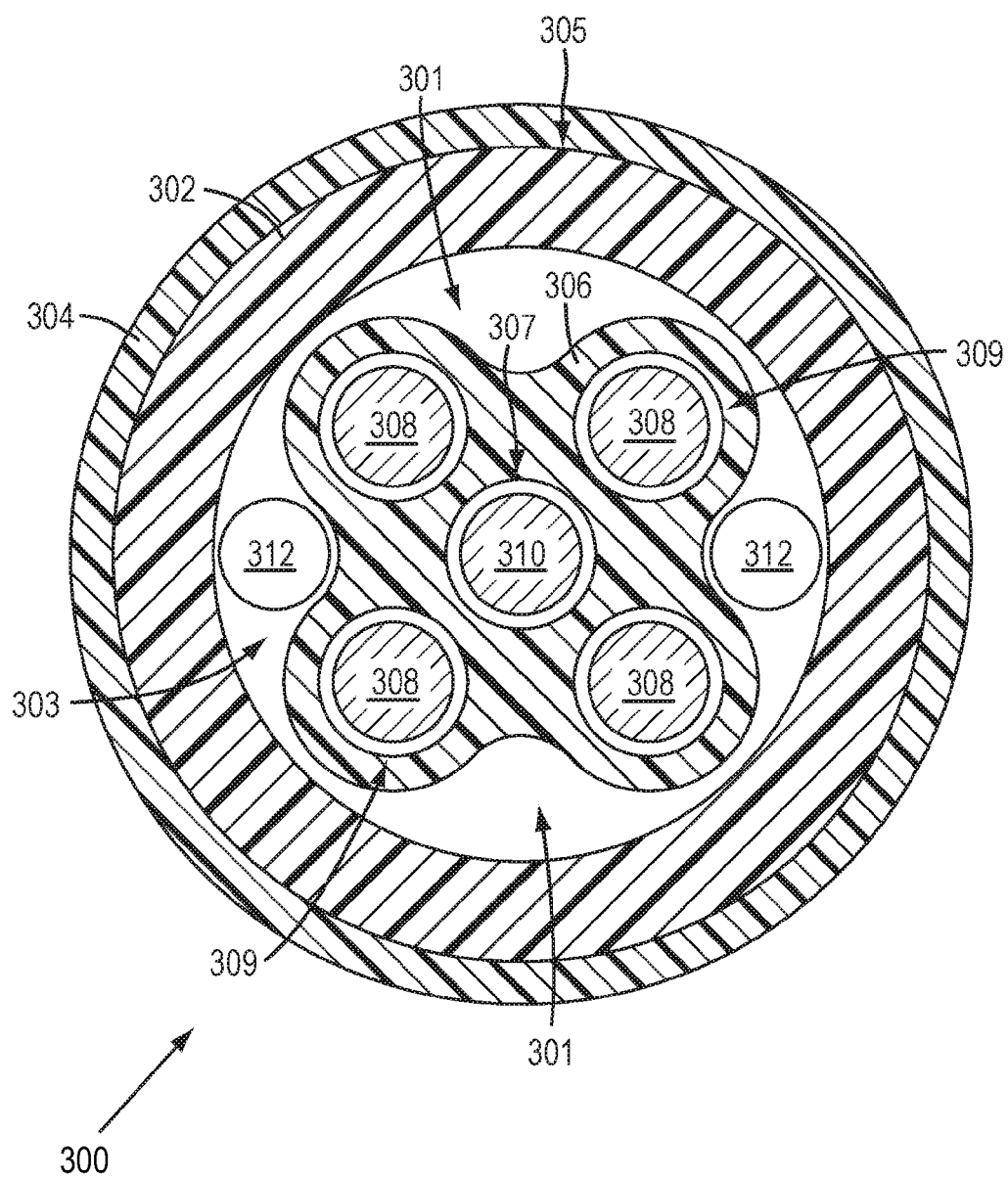
FIG. 4 is a cross-sectional view of the shaft of FIG. 3 taken along line 4-4.

Some shaft configurations utilize multiple parts to provide a shaft that is flexible, such as to facilitate passing an instrument through a curved cannula, but also stiff, such as to support an end effector. Further, the shaft may include paths to route cabling and other instrument control mechanisms from a proximal end to a distal end. Turning to FIG. 3, an exploded view of an exemplary embodiment of a shaft 300 for a surgical instrument is shown. Shaft 300 may include an outer tube 302 and a channeled insert 306 sized to be contained inside of the outer tube 302. Turning to FIG. 4, which is a cross-sectional view along line 4-4 in FIG. 3, channeled insert 306 may include a lumen 307 for a drive member 310 connecting a force transmission mechanism to an end effector of the surgical instrument, as discussed in the exemplary embodiments of FIGS. 1 and 2. For instance, drive member 310 may be a drive element rod, such as when the force transmission mechanism is a push-pull mechanism to actuate the end effector. Channeled insert 306 may be provided within outer tube 302 to support and locate drive member 310 within outer tube 302. According to an exemplary embodiment, outer surface 305 of first tube 302 may form an outer surface of the shaft.

Outer tube 302 may be constructed to provide a degree of stiffness and flexibility to shaft 300. For instance, outer tube 302 may be made of a relatively durable and stiff material that is relatively flexible. For example, outer tube 302 may comprise polyether ether ketone (PEEK) or other similar materials used in the art for the tubes of surgical instrument shafts. The insert 306 may be constructed so that insert 306 is more compliant and flexible than outer tube 302. For instance, it may be desirable for insert 306 to be more compliant and flexible than outer tube 302 to facilitate insertion of insert 306 within outer tube 302. To accomplish this, insert 306 may be made of a material that is more compliant than the material of outer tube 302. For example, insert 306 may comprise fluorinated ethylene propylene (FEP).

Outer tube 302 and insert 306 may be sized and arranged relative to one another to provide lumens within the instrument shaft 300 between outer tube 302 and insert 306. As shown in the exemplary embodiment of FIG. 4, outer tube 302 and insert 306 may be configured to provide one or more lumens 301 between outer tube 302 and insert 306. Lumen 301 may be used, for instance, as a passage for cleaning fluid to flush an interior of shaft 300 during a procedure to clean a surgical instrument. According to an exemplary embodiment, shaft 300 may include one or more conduits 312 to provide a flux to an end effector of a surgical instrument. In such embodiments, tube 302 and insert 306 may provide one or more lumens 303 for the one or more conduits 312. A flux may be, for example, a form of energy, suction, irrigation fluid, or other flux used with surgical instruments. For instance, if a surgical instrument is an electrosurgical instrument, such as for cauterization procedure, the one or more conduits 312 may be wires to provide electrical energy to an end effector.

Because insert 306 is relatively compliant and flexible, particularly in comparison to outer tube 302, insert 306 may be altered to increase the stiffness of insert 306. For instance, insert 306 may include one or more structures to increase the stiffness of insert 306. As shown in the exemplary embodiment of FIGS. 3 and 4, one or more wires 308 may be inserted within lumens 309 of insert 306 to increase the stiffness of insert 306. According to an exemplary embodiment, wires 308 may be made of a material having a higher stiffness than the material of insert 306. For example, wires 308 may be made of a metal. In another example, wires 308 may be made of a stainless steel, such as type 304 stainless steel. Stiffening wires may extend the length of shaft 300, such as from proximal end 223 to distal end 224, as shown in the exemplary embodiment of FIG. 2. As shown in the exemplary embodiment of FIGS. 3 and 4, shaft 300 may include four stiffening wires 308, although shaft 300 is not limited to this number of wires 308 and the number and type of stiffening structures may be selected as desired.

According to an exemplary embodiment, shaft 300 may include a sheath 304 located on an outer surface of first tube 302. Sheath 304 may be provided to affect the coefficient of friction of shaft 300, such as by providing a smooth surface that facilitates insertion of an instrument within a cannula. In various exemplary embodiments, sheath 304 may be made of ethylene tetrafluoroethylene (ETFE) or other sheath materials that are used in the art.

A surgical instrument shaft 300 having a construction shown in the exemplary embodiment of FIGS. 3 and 4 can be both compliant enough to be advanced and withdrawn through a curved cannula, while being stiff enough to support the functions of an end effector connected to a distal end of shaft 300. However, shaft 300 includes numerous components, which can be made of different materials. In addition, manufacture of shaft 300 may require numerous steps. As a result, shaft 300 may be relatively costly to manufacture due to the complexity of its production process and the different materials utilized.

Another consideration for the shaft 300 of the exemplary embodiment of FIGS. 3 and 4 is the ease of controlling the properties of shaft 300. Manufacturing processes and tolerances may make manufacture of shaft 300 relatively difficult, particularly when shaft 300 includes multiple pieces, such as outer tube 302, insert 306, and wires 308. For instance, manufacturing processes and tolerances of the dimensions of shaft components in both a radial direction and an axial direction along the length of the shaft may affect the overall stiffness of the shaft.

In view of these considerations, various exemplary embodiments contemplate a surgical instrument having a shaft that is relatively easy and inexpensive to manufacture and exhibits an overall stiffness that enhances control of the instrument during use and is substantially uniform from one shaft to another. Various exemplary embodiments may provide a surgical instrument that exhibits enhanced motion control and minimal unintended movement of an end effector, such as in directions 230, 232 shown in the exemplary embodiment of FIG. 2, during the use of the end effector of the instrument.

Figure 5:
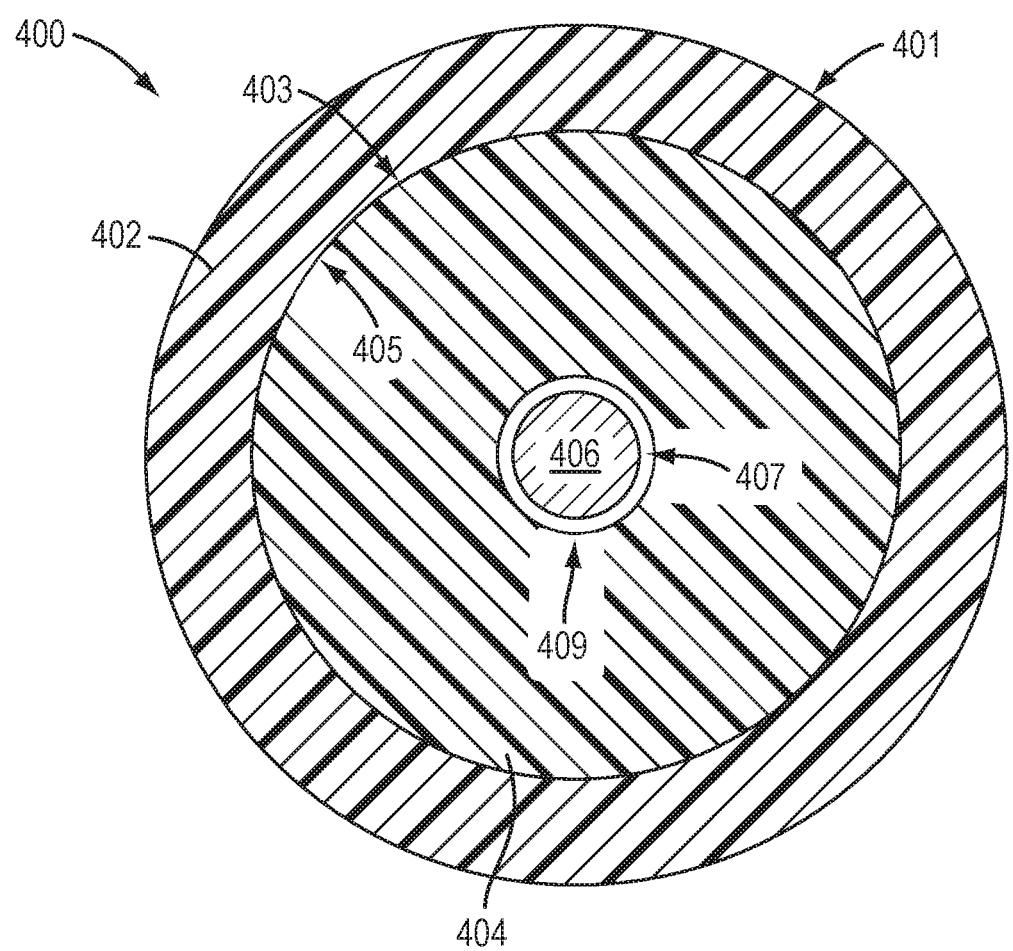
FIG. 5 is a cross-sectional view of an exemplary embodiment of a shaft of a surgical instrument.

Turning to FIG. 5, an exemplary embodiment of a surgical instrument shaft 400 is shown in cross-section. Shaft 400 may be used for an instrument discussed in the exemplary embodiments of FIGS. 1 and 2. As shown in FIG. 5, shaft 400 may include an outer tube 402 and an inner tube 404.

According to an exemplary embodiment, shaft 400 may have a body that is provided by inner tube 404 and outer tube 402. For instance, the body of shaft 400 may extend between an inner surface 409 of inner tube 404 to an outer surface 401 of outer tube 402. Thus, inner surface 409 may form an inner surface of the body of shaft 400 and outer surface 401 may form an outer surface of the body of shaft 400. According to an exemplary embodiment, each of inner tube 404 and outer tube 402 may be made by extruding a material to form a hollow cylinder, as shown in FIG. 5.

According to an exemplary embodiment, inner tube 404 may have a wall thickness that is substantially the same as the wall thickness of outer tube 402. According to another example embodiment, inner tube 404 and outer tube 402 have different wall thicknesses. For instance, inner tube 404 may have a greater wall thickness or a smaller wall thickness than outer tube 402.

Outer tube 402 and inner tube 404 may each have a form of a hollow cylinder, according to an exemplary embodiment. As shown in the exemplary embodiment of FIG. 5, outer tube 402 may be continuously solid between its inner surface 403 and its outer surface 401 and thus lack any lumen (i.e., be lumenless). Similarly, inner tube may be solid and lack any lumen between its outer surface 405 and its inner surface 409, as shown in the exemplary embodiment of FIG. 5.

Inner tube 404 may include a lumen 407 that is configured to receive a drive member 406 connecting a force transmission mechanism to an end effector of the surgical instrument, as discussed in the exemplary embodiments of FIGS. 1 and 2. An inner surface 409 of inner tube 404 that forms lumen 407 can be in contact with drive member 406, according to an exemplary embodiment. According to an exemplary embodiment, lumen 407 may have a diameter ranging from about 0.030" to about 0.050". According to another exemplary embodiment, lumen 407 may have a diameter ranging from about 0.035" to about 0.045". According to an exemplary embodiment, a diameter of shaft 400 may be about 5 to about 5.5 times the diameter of lumen 407.

According to an exemplary embodiment, an outer surface 401 of outer tube 402 may form an outer surface of shaft 400. For instance, outer surface 401 may be uncovered or otherwise exposed to a surrounding environment. As shown in the exemplary embodiment of FIG. 5, outer surface 401 may have a substantially circular cross-section. According to an exemplary embodiment, shaft 400 may consist of drive member 406, inner tube 404, and outer tube 402.

Tubes 402, 404 may be provided, for example, as hollow cylinders, as shown in the exemplary embodiment of FIG. 5, that have similar shapes and are concentric. According to an exemplary embodiment, an inner surface 403 of outer tube 402 and an outer surface 405 of inner tube 404 may have substantially the same radius of curvature. Although inner tube 404 and outer tube 402 are in contact with one another, inner tube 404 and outer tube 402 may be configured to move relative to one another to facilitate bending of shaft 400. For instance, inner tube 404 and outer tube 402 may be configured to slide relative to one another, such as along the proximal-distal direction shown in the exemplary embodiment of FIG. 2, when shaft 400 is bent.

According to an exemplary embodiment, tubes 402, 404 may have similar or substantially the same stiffness values. As a result, inner tube 404 may function as a stiffening tube for outer tube 402 and may provide a sufficient stiffness to the shaft so as to enable support of the end effector as discussed above. Utilizing the inner tube 404 as a mechanism for stiffening the outer tube 402 can reduce the number of other additional stiffening members that may be used and the overall number of components of the surgical instrument shaft.

According to an exemplary embodiment, inner tube 404 and outer tube 402 may comprise the same material, such as, for example, PEEK. Use of the same or similar materials that provide sufficient stiffness properties for both the inner tube 402 and outer tube 404 may further provide the shaft with an overall stiffness that is substantially uniform from one shaft to another during a manufacturing process.

Figure 6:
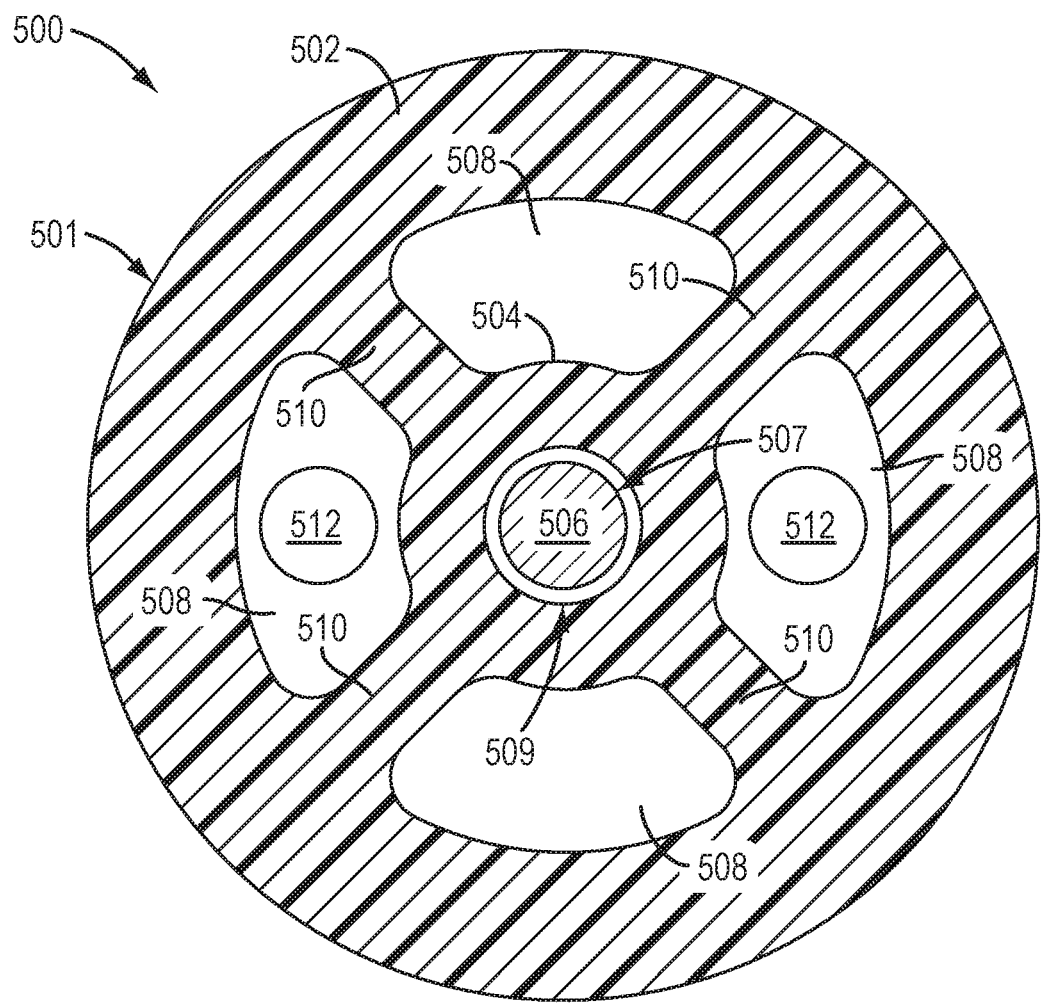
FIG. 6 is a cross-sectional view of another exemplary embodiment of a shaft of a surgical instrument.

Turning to FIG. 6, an exemplary embodiment of a shaft 500 of a surgical instrument is shown in cross section. Shaft 500 may include an outer tube 502 and an inner tube 504. Inner tube 504 may include a lumen 507 for a drive member 506 connecting a force transmission mechanism to an end effector of the surgical instrument, as discussed in the exemplary embodiments of FIGS. 1 and 2. An inner surface 509 of inner tube 504 that defines lumen 507 may be in contact with drive member 506, according to an exemplary embodiment.

Outer tube 502 and inner tube 504 may be connected by a plurality of ribs 510. As shown in the exemplary embodiment of FIG. 6, ribs 510, inner tube 504, and outer tube 502 may define one or more lumens 508. Lumens 508 may be used, for example, for flushing fluid in a cleaning operation. In another example, lumens 508 may serve as passages, such as for one or more conduits 512 to provide a flux to an end effector of a surgical instrument. According to an exemplary embodiment, an outer surface 501 of outer tube 502 may define an outer surface of shaft 500. Further, according to an exemplary embodiment, shaft 500 may consist of inner tube 504, outer tube 502, at least one rib 510, at least one lumen 508, and drive member 506. According to another exemplary embodiment, shaft 500 may include inner tube 504, outer tube 502, at least one rib 510, at least one lumen 508, at least one conduit 512, and drive member 506.

A body of shaft 500 may be formed by inner tube 504, outer tube 502, and ribs 510. To provide an instrument shaft that advantageously includes fewer components, is less difficult to manufacture, and is less costly to manufacture, instrument shaft 500 (not including drive member 506) may have a single piece construction. Thus, the body of shaft 500 formed by inner tube 504, outer tube 502, and ribs 510 may be formed as a single piece. According to an exemplary embodiment, the body formed by inner tube 504, outer tube 502, and ribs 510 may be defined by a single piece formed in an extrusion process. According to an exemplary embodiment, the body formed by inner tube 504, outer tube 502, and ribs 510 may be made of the same material. For instance, the body of shaft 500 may be formed from a single material between inner surface 509 and outer surface 501. Thus, inner surface 509 may form an inner surface of the body of shaft 500 and outer surface 501 may form an outer surface of the body of shaft 500. According to an exemplary embodiment, an outer surface 501 of outer tube 502 may form an outer surface of shaft 500. For instance, outer surface 501 may be uncovered or otherwise exposed to a surrounding environment. As shown in the exemplary embodiment of FIG. 6, outer surface 501 may have a substantially circular cross-section.

The stiffness of shaft 500 may be varied, for example, by altering the dimensions of shaft 500. For instance, a thickness of inner tube 504, outer tube 502, and/or ribs 510 may be varied to affect the stiffness of shaft 500. Inner tube 504 may have a thickness of, for example, about 0.095 inches to about 0.105 inches. Outer tube 502 may have a thickness of, for example, about 0.030 inches to about 0.040 inches. Ribs 510 may have a thickness of about 0.020 inches to about 0.030 inches. According to an exemplary embodiment, the material of inner tube 504, outer tube 502, and ribs 510 may be selected to provide a desired stiffness for shaft 500. Another method of controlling the stiffness of shaft 500 is selecting the number of ribs 510, according to an exemplary embodiment. As shown in the exemplary embodiment of FIG. 6, shaft 500 may include four ribs 510. However, a shaft for a surgical instrument may include, for example three ribs, five ribs, or other numbers of ribs.

Further, although shaft 500 may lack stiffening wires, which may be made out of a material having a relatively high stiffness, such as a metal, and thus shaft 500 may be expected to have a lower overall stiffness, shaft 500 has a sufficient stiffness but advantageously exhibits an overall stiffness that is more easily controlled and more uniform from one shaft to another in comparison to shafts including stiffening wires. As a result, shaft 500 advantageously enhances movement control and minimizes movement of end effector during actuation of the end effector, such as in directions 230, 232 discussed above in regard to FIG. 2.

Figure 7:
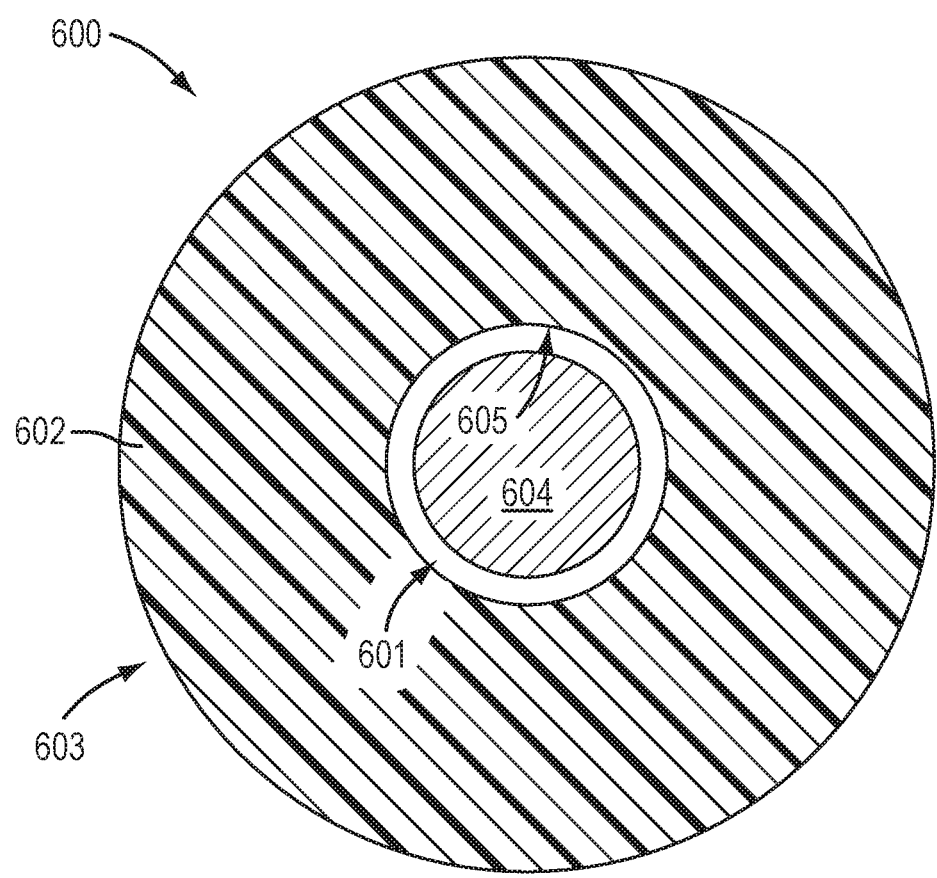
FIG. 7 is a cross-sectional view of yet another exemplary embodiment of a shaft of a surgical instrument.

Turning to FIG. 7, an exemplary embodiment of a shaft 600 of a surgical instrument is shown in cross section. Shaft 600 may be defined by a single tube 602 that includes a lumen 601 for a drive member 604 connecting a force transmission mechanism to an end effector of the surgical instrument, as discussed in the exemplary embodiments of FIGS. 1 and 2. According to an exemplary embodiment, lumen 601 may be utilized during a cleaning operation by flushing material through lumen 601. An inner surface 605 of tube 602 that defines lumen 601 may be in contact with drive member 604, according to an exemplary embodiment.

According to an exemplary embodiment, tube 602 may be provided as a single piece tube. Thus, a body of shaft 600 may be formed by tube 602. Further, as shown in the exemplary embodiment of FIG. 7, tube 602 may be a continuously solid hollow cylinder between the outer surface 603 of tube 602 and the inner surface 605 of tube 602 and thus lack any lumen (i.e., be lumenless). In other words, tube 602 may be a hollow cylinder that includes a single lumen, namely lumen 601 for drive member 604. According to an exemplary embodiment, outer surface 603 of tube 602 may define an outer surface of shaft 600. For instance, outer surface 603 may be uncovered or otherwise exposed to a surrounding environment. As shown in the exemplary embodiment of FIG. 6, outer surface 501 may have a substantially circular cross-section.

According to an exemplary embodiment, tube 602 may be made from a single material. Thus, a body of shaft 600 may be made from a single material between inner surface 601 and outer surface 603. Further, inner surface 601 may form an inner surface of the body of shaft 600 and outer surface 603 may form an outer surface of the body of shaft 600. According to an exemplary embodiment, tube 602 may be made by extruding a single material to form a hollow cylinder, as shown in FIG. 7. According to an exemplary embodiment, shaft 600 may consist of tube 602 and drive member 604.

By providing tube 602 with a single piece construction, a shaft 600 may be advantageously provided that minimizes movement of an end effector during actuation of the end effector, such as in directions 230, 232 discussed above in regard to FIG. 2. Further, although shaft 600 may lack stiffening wires, which may be made out of a material that has a relatively high stiffness, such as a metal, shaft 600 has a sufficient overall stiffness that is more easily controlled and more uniform from one shaft to another in comparison to shafts including stiffening wires.

As noted above, materials for a shaft may be selected to affect the stiffness of a shaft. According to an exemplary embodiment, inner tube 404 and outer tube 402 of FIG. 5; inner tube 504, outer tube 502, and ribs 510 of FIG. 6; and tube 602 of FIG. 7 may be made of PEEK. With regard to the exemplary embodiments of FIGS. 6 and 7, the single piece constructions provided by inner tube 504, outer tube 502, and ribs 510 in FIG. 6 and the single piece construction provided by tube 602 in FIG. 7 may be provided by a single piece comprising PEEK. PEEK may be selected as the material to form the tubes of these exemplary embodiments because of its desirable stiffness values and biocompatibility. For instance, PEEK may be selected instead of FEP for these embodiments because FEP is more compliant and deformable, which could lead to movement of an end effector, such as in directions 230, 232 discussed above in regard to FIG. 2, if the FEP deformed.

According to an exemplary embodiment, PEEK may be in an annealed condition. Further, PEEK may be unfilled, according to an exemplary embodiment. Unfilled PEEK may have a tensile modulus of, for example, about 535,000 psi to about 545,000 psi. According to another exemplary embodiment, PEEK may include one or more fillers, such as, for example, glass fiber reinforcement or carbon fiber reinforcement. PEEK that includes a glass fiber reinforcement filler may have a tensile modulus of, for example, about 1,650,000 psi to about 1,750,000 psi. PEEK that includes a carbon fiber reinforcement filler may have a tensile modulus of, for example, about 3,600,000 psi to about 3,950,000 psi. PEEK may be available from Victrex® PLC of Lancashire UK. Exemplary commercial grades of unfilled PEEK available from Victrex® PLC include PEEK 90G, PEEK 151G, PEEK 151G, PEEK 381G, PEEK 450G, and PEEK 450G903. Exemplary commercial grades of filled PEEK available from Victrex® PLC include PEEK 90GL30, PEEK 150GL30, PEEK 450GL30, PEEK 90CA30, PEEK 150CA30, PEEK 90CA30, PEEK 150CA30, PEEK 450CA30, and PEEK 90HMF20. According to an embodiment, the material used for a shaft may include a material to increase the lubricity of the shaft. For instance, the material of the shaft may include, for example, about 5% to about 10% of PTFE and/or perfluoropolyether (PFPE). The addition of the material to increase lubricity of a shaft may advantageously avoid the need for an additional sheath to be placed over an exterior surface of the shaft to lower the coefficient of friction of the outer surface to minimize friction and wear.

Other materials may be used for the exemplary embodiments of FIGS. 5-7. Other materials include, for example, acetal, nylon, polyester, and sulfone plastics. Materials selected for the exemplary embodiments of FIGS. 5-7 may be selected to provide a shaft of a surgical instrument with a desired stiffness. In another example, materials may be selected that are weldable to other components of a surgical instrument. Further, the materials may be selected to minimize damage and wear to an instrument shaft. For instance, material(s) may be selected so that an instrument exhibits substantially no damage after applying 2 lbf to a distal tip of the instrument in a direction normal to a roll axis of the instrument.

According to an exemplary embodiment, a shaft of a surgical instrument lacking stiffening wires, such as according to the exemplary embodiments of FIGS. 5-10, may be configured to have an axial stiffness ranging from about 900 lbs/in to about 1250 lbs/in and a bending stiffness ranging from about 50 lbs*in$^2$ to about 65 lbs*in$^2$, according to calculations. In contrast, a shaft configured according to the exemplary embodiment of FIG. 4 to include stiffening wires, may have an axial stiffness ranging from about 400 to about 5000 lb/in and a bending stiffness ranging from about 20 to about 500 lbs*in$^2$, depending on the stiffening wire to tube interface. Although the maximum calculated stiffness for shafts lacking stiffening wires is lower, this stiffness is not only sufficient but is also advantageously more uniform and consistent from one shaft to another.

Figure 11:
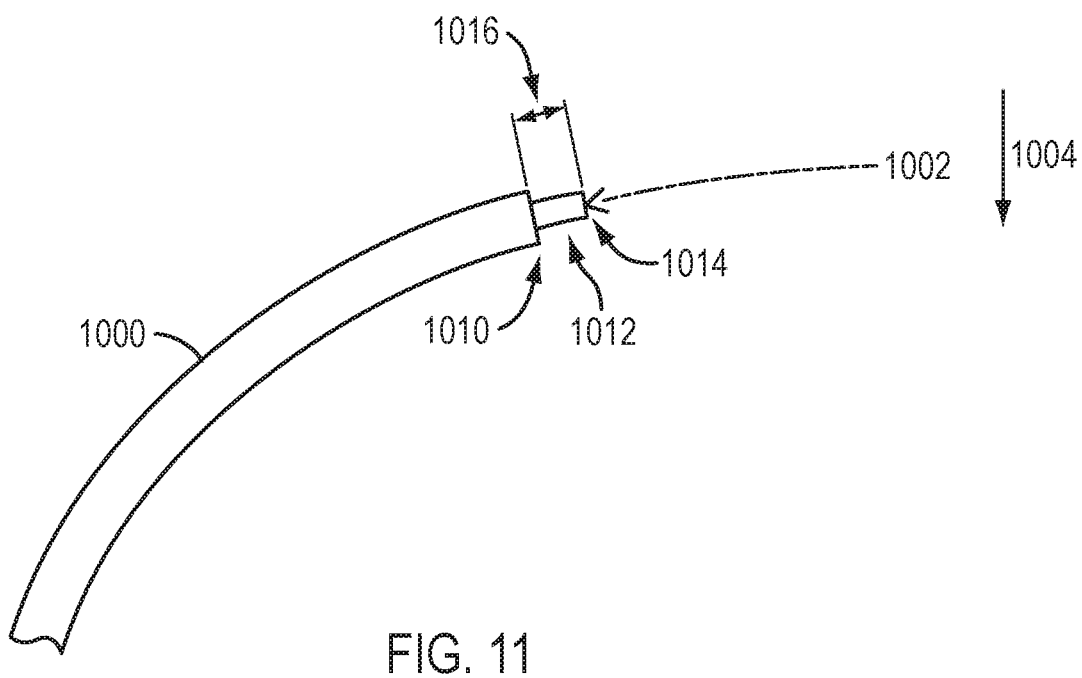
FIG. 11 is a schematic side view of a surgical instrument inserted to a maximum distance within a curved cannula, according to an exemplary embodiment.
Figure 12:
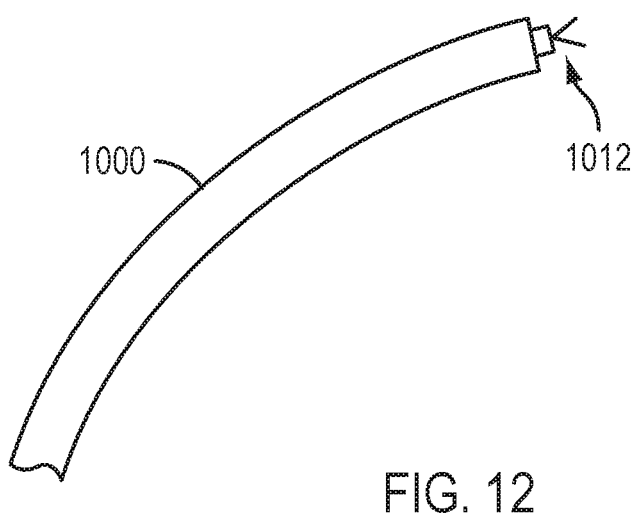
FIG. 12 is a schematic side view of a surgical instrument inserted to a minimum distance within a curved cannula, according to an exemplary embodiment.

According to an exemplary embodiment, a shaft of a surgical instrument may be configured so that a force required to advance or withdraw the instrument through a cannula is no more than 5 lbf. Turning to FIG. 11, an exemplary embodiment of a surgical instrument is shown inserted within a curved cannula 1000 so that shaft 1012 of the instrument has reached maximum insertion. When advanced to maximum insertion, a distal end 1014 of instrument shaft 1012 may extend a distance 1016 beyond a distal end 1010 of cannula 1000 ranging, for example, from about 5 inches to about 11 inches. FIG. 12 shows an exemplary embodiment of the instrument shaft 1012 withdrawn to a minimum insertion within cannula 1000. A minimum insertion distance between a distal end 1014 of instrument shaft 1012 and a distal end 1010 of cannula 1000 may range, for example, from about 0.125 inches to about 0.250 inches. According to an exemplary embodiment, a shaft of a surgical instrument may be configured so that no more than about 2.5 lbf is required to advance an instrument from a minimum insertion distance to a maximum insertion distance within a curved cannula.

The stiffness of a shaft of a surgical instrument may be evaluated, for example, by measuring movement of an end effector when the end effector is actuated. For instance, when an instrument has been advanced to the maximum insertion position shown in the exemplary embodiment of FIG. 11, a weight may be hung from the distal end 1014 of the shaft 1012 and a deflection 1004 of the shaft 1012 relative to a longitudinal axis 1002 of the cannula 1000 may be determined. According to an exemplary embodiment, when a one pound weight is hung from the distal end 1014 of shaft 1012, a maximum deflection 1004 of about 1.5 inches occurs relative to the longitudinal axis 1002 of cannula 1000.

As discussed above, a shaft of a surgical instrument may be provided by a single piece tube, as discussed in the exemplary embodiments of FIGS. 6 and 7. However, it may be advantageous to provide a shaft with a sheath on an outer surface of the tube. For instance, providing a sheath on the outer surface of a tube may advantageously provide a lower coefficient of friction, which reduces friction and wear when advancing and withdrawing an instrument through a cannula. According to an exemplary embodiment, a sheath may be made of a material having a lower coefficient of friction than a tube material that the sheath is located upon. A sheath may comprise, for example, ETFE or other sheath materials used in the art.

Figure 8:
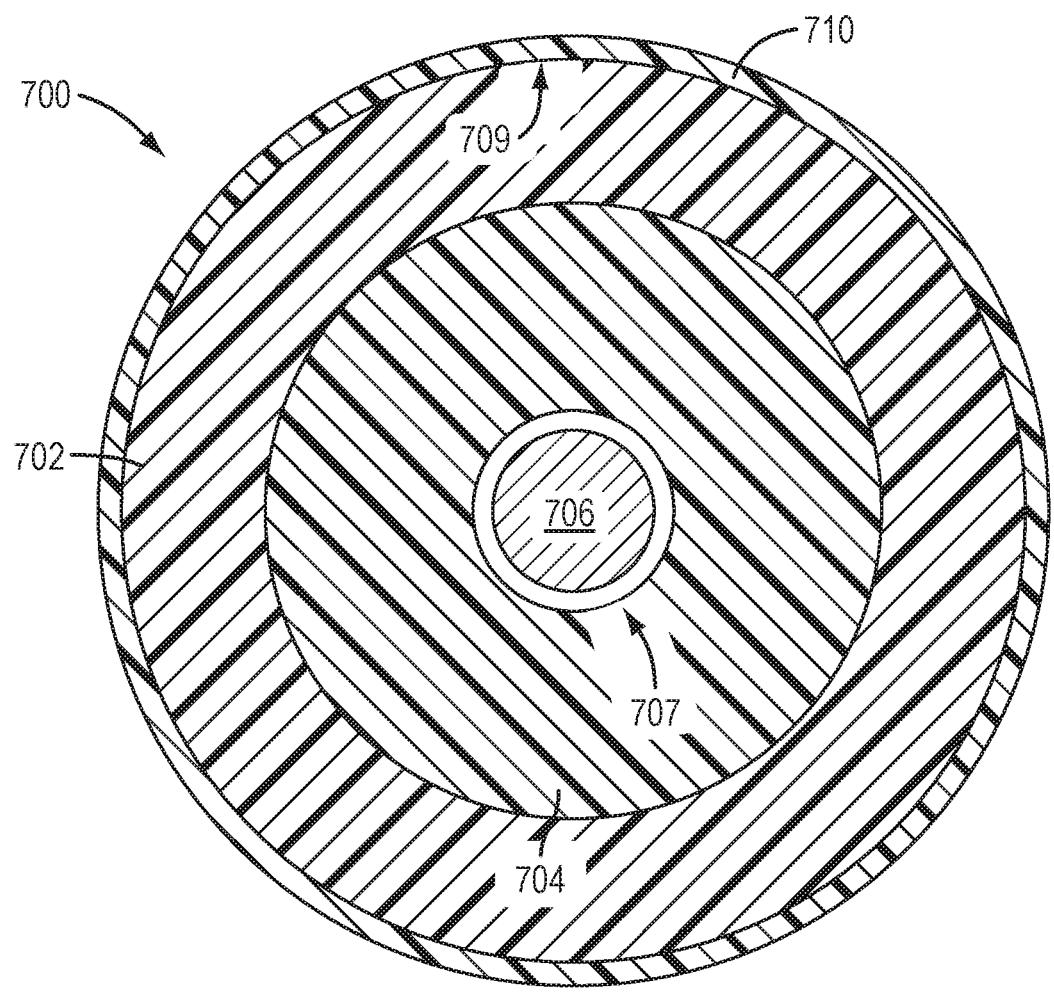
FIG. 8 is a cross-sectional view of an exemplary embodiment of a sheathed shaft of a surgical instrument.

Turning to FIG. 8, an exemplary embodiment of a shaft 700 is shown that includes an outer tube 702 and an inner tube 704 that forms a lumen 707 for a drive member 706. Shaft 700 may be formed according to the exemplary embodiment of FIG. 5, except that a sheath 710 is provided on an outer surface 709 of outer tube 702. According to an exemplary embodiment, outer surface 709 may form an outer surface of shaft 700, with sheath 710 provided on outer surface 709. As shown in the exemplary embodiment of FIG. 9, a shaft 800 may include an outer tube 802, an inner tube 804 that forms a lumen 807 for a drive member 806, one or more lumens 808, and ribs 810. Shaft 800 may be formed according to the exemplary embodiment of FIG. 6, except that a sheath 820 is provided on an outer surface 803 of outer tube 802. According to an exemplary embodiment, outer surface 803 may form an outer surface of shaft 800, with sheath 820 provided on outer surface 803. Turning to FIG. 10, an exemplary embodiment of a shaft 900 is shown that includes a single tube 902 that forms a lumen 901 for a drive member 904. Shaft 900 may be formed according to the exemplary embodiment of FIG. 7, except that a sheath 910 is provided on an outer surface 903 of tube 902. According to an exemplary embodiment, outer surface 903 may form an outer surface of shaft 900, with sheath 910 provided on outer surface 903.

Figure 9:
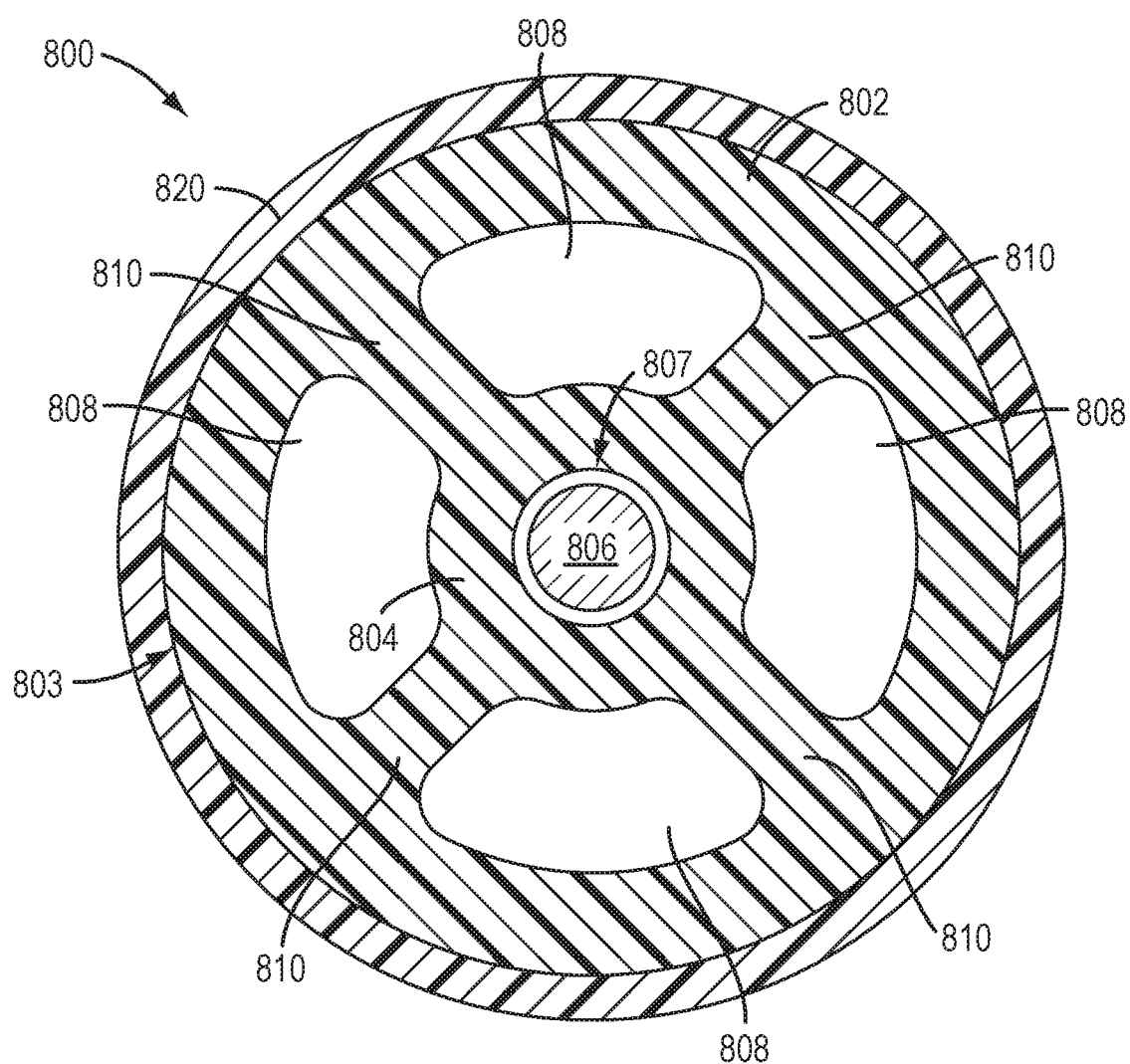
FIG. 9 is a cross-sectional view of another exemplary embodiment of a sheathed shaft of a surgical instrument.
Figure 10:
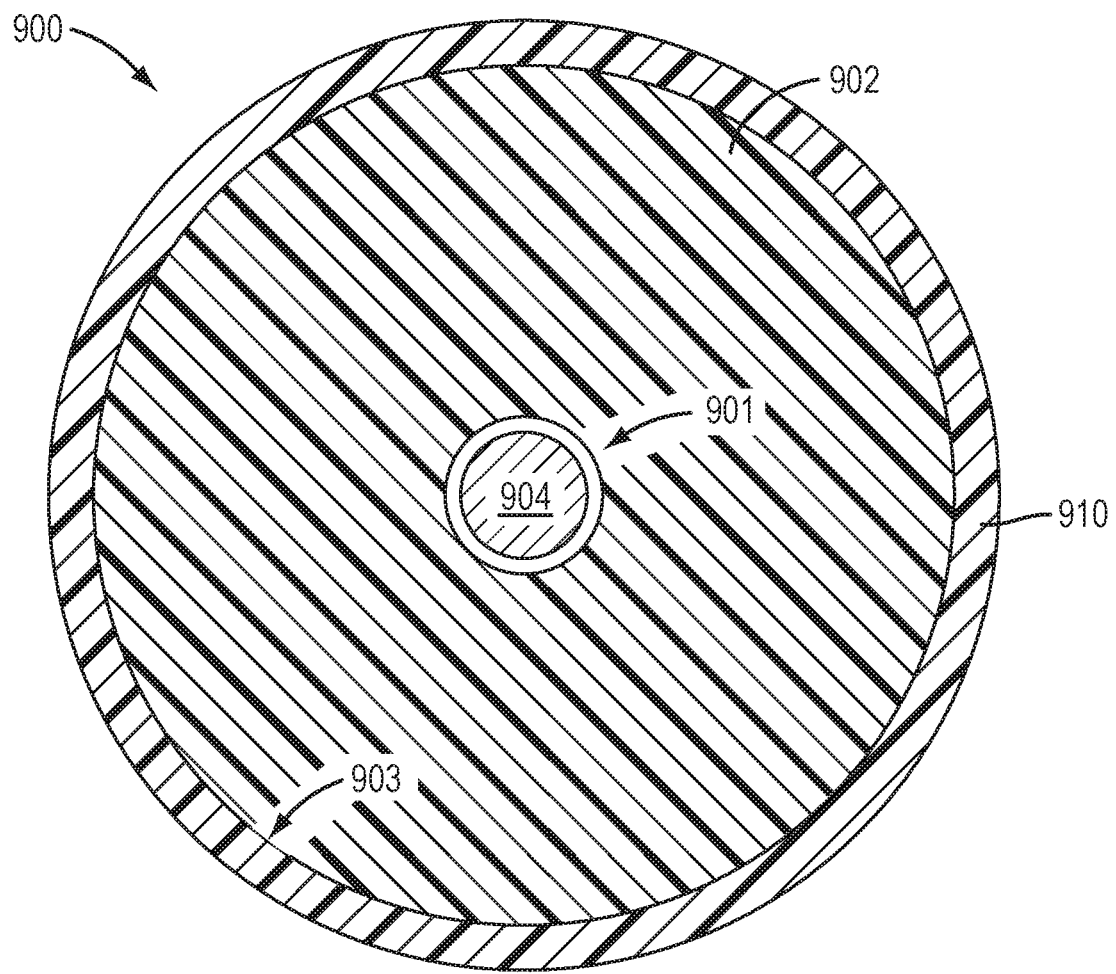
FIG. 10 is a cross-sectional view of yet another exemplary embodiment of a sheathed shaft of a surgical instrument.

According to an exemplary embodiment, when a shaft of a surgical instrument is provided with a sheath, such as in the exemplary embodiments of FIGS. 8-10, dimensions of the shaft may be redesigned to accommodate the sheath. For instance, the outer diameter of the shaft may remain the same whether a sheath is present or absent so that the stiffness of the shaft is maximized while permitting the shaft to fit through a cannula. Therefore, if a sheath is provided, the dimensions of the tube and other components of the shaft may be reduced. For instance, in the exemplary embodiment of FIG. 5, the radial thickness of outer tube 402 and/or inner tube 404 may be reduced. In another instance, in the exemplary embodiment of FIG. 6, at least one of the radial thickness of inner tube 504, the radial thickness of outer tube 502, and the length of ribs 510 may be reduced. In another instance, in the exemplary embodiment of FIG. 7, the radial thickness of tube 602 may be reduced.

Figure 13:
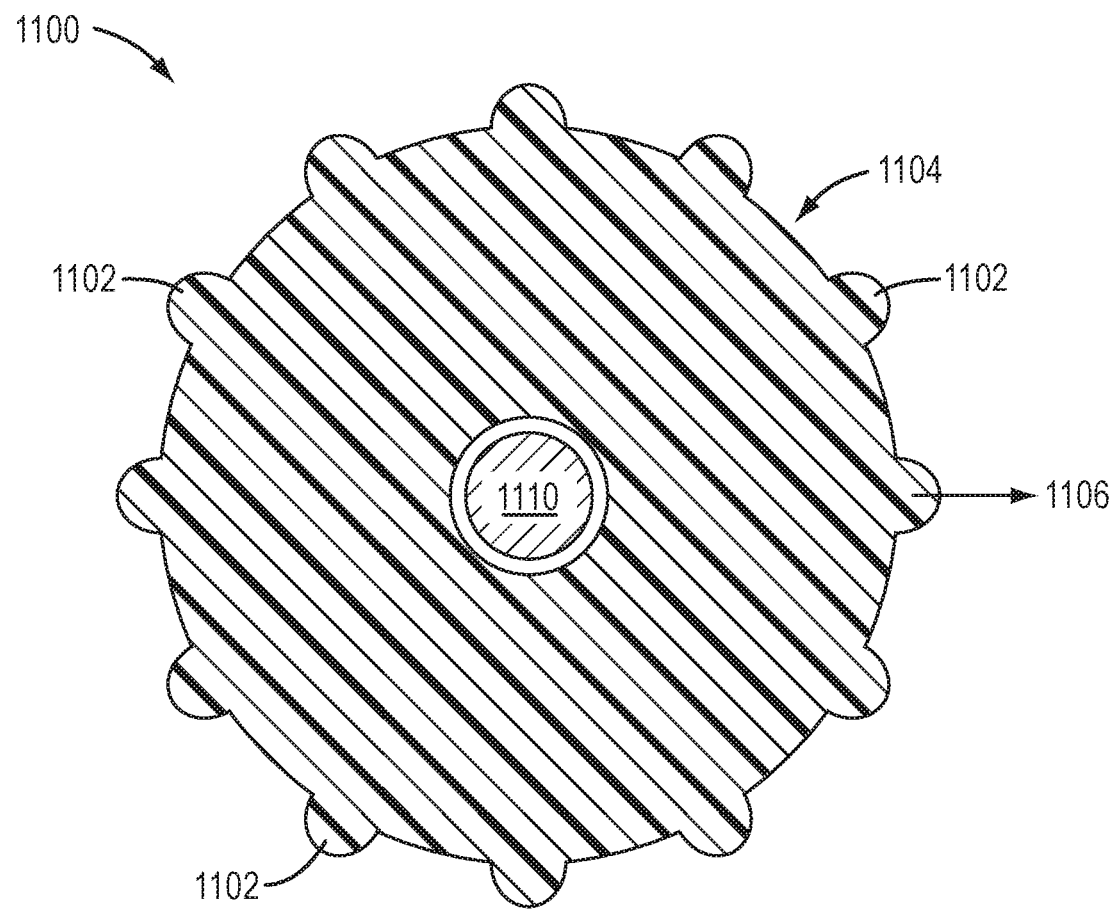
FIG. 13 is a cross-sectional view of another exemplary embodiment of a shaft of a surgical instrument.

Although the exemplary embodiments of FIGS. 4-7 show shafts having a substantially smooth outer surface, shafts may have other surface configurations. Turning to FIG. 13, a cross-sectional view of an exemplary embodiment of a shaft 1100 is shown that includes a plurality of projections 1102 on the outer surface 1104 of shaft 1100. Shaft 1100 may include a drive member 1110 connecting a force transmission mechanism to an end effector of the surgical instrument, as discussed in the exemplary embodiments of FIGS. 1 and 2. Further, shaft 1100 may be constructed according to any of the exemplary embodiments of FIGS. 5-7. As shown in the exemplary embodiment of FIG. 13, projections 1102 may extend a non-zero distance along a radial direction 1106 from outer surface 1104. By providing projections 1102, the amount of contact area between shaft 1100 and an inner surface of a curved cannula may be reduced, which advantageously reduces friction and wear. According to an exemplary embodiment, projections 1102 may be sufficient to reduce friction to a degree that shaft 1100 does not require a sheath to minimize friction and wear. Further, projections 1102 are not limited to what is shown in the exemplary embodiment of FIG. 13. For instance, projections 1102 may be provided in fewer or greater numbers, be spaced closer or further apart in a uniform or non-uniform spacing, and/or may have different shapes.

By providing a surgical instrument according to the exemplary embodiments discussed above, a surgical instrument may be advantageously provided that is simpler to manufacture, less costly to manufacture, and provides enhanced properties. For instance, a shaft of the surgical instrument may minimize movement of an end effector during actuation of the end effector, such as in directions 230, 232 discussed above in regard to FIG. 2. Further, although the shaft may lack stiffening wires made of a material having a relatively high stiffness, the shaft has a sufficient overall stiffness that is more easily controlled and more uniform from one shaft to another in comparison to shafts that include stiffening wires.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

In this description, an actively flexible piece may be bent by using forces inherently associated with the piece itself. For example, one or more tendons may be routed lengthwise along the piece and offset from the piece's longitudinal axis, so that tension on the one or more tendons causes the piece to bend. Other ways of actively bending an actively flexible piece include, without limitation, the use of pneumatic or hydraulic power, gears, electroactive polymer, and the like. A passively flexible piece is bent by using a force external to the piece. An example of a passively flexible piece with inherent stiffness is a plastic rod or a resilient rubber tube. An actively flexible piece, when not actuated by its inherently associated forces, may be passively flexible. A single component may be made of one or more actively and passively flexible portions in series.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical instrument, comprising:
a shaft body comprising:
a proximal end and a distal end,
a length from the proximal end to the distal end,
a longitudinal axis defined by the proximal and distal ends,
an outer cylindrical tube,
an inner cylindrical tube positioned concentrically within and spaced from the outer cylindrical tube,
a plurality of ribs extending radially from an outer circumferential surface of the inner cylindrical tube to an inner circumferential surface of the outer cylindrical tube, and
a plurality of passages extending along the length of the shaft body from the proximal end to the distal end and disposed around the longitudinal axis,
wherein the plurality of ribs connect the outer cylindrical tube and the inner cylindrical tube,
wherein the plurality of passages and the plurality of ribs are alternatingly disposed around the longitudinal axis of the shaft,
wherein each passage of the plurality of passages is defined by a first pair of opposing surfaces and a second pair of opposing surfaces,
wherein the first pair of opposing surfaces comprises surfaces of consecutively positioned ribs of the plurality of ribs,
wherein the second pair of opposing surfaces comprises the inner circumferential surface of the outer cylindrical tube and the outer circumferential surface of the inner cylindrical tube,
wherein each passage of the plurality of passages has a same cross-sectional area,
wherein the cross-sectional area of each passage of the plurality of passages is larger than a cross-sectional area of each rib, and
wherein the outer cylindrical tube, the inner cylindrical tube, and the plurality of ribs are an integral structure made from a single material;
a force transmission mechanism coupled to the proximal end of the shaft body;
a surgical end effector coupled to the distal end of the shaft body; and
a drive member operably coupled to the force transmission mechanism and the end effector, the drive member extending from the force transmission mechanism through the inner cylindrical tube to the end effector.

2. The surgical instrument of claim 1, wherein the shaft body is sufficiently flexible to pass through a curved cannula.

3. The surgical instrument of claim 1, further comprising an electrosurgical flux transmission conduit extending through a first passage of the plurality of passages.

4. The surgical instrument of claim 3, wherein the electrosurgical flux transmission conduit is spaced from the first and second pairs of opposing surfaces of the first passage.

5. The surgical instrument of claim 1, wherein the plurality of passages consists of four passages.

6. The surgical instrument of claim 1, wherein the single material of the outer cylindrical tube, the inner cylindrical tube, and the plurality of ribs is polyether ether ketone material.

7. The surgical instrument of claim 1, wherein the shaft body is a single extruded piece.

8. The surgical instrument of claim 1, wherein the drive member is located within the inner cylindrical tube.

9. The surgical instrument of claim 1, wherein the surgical instrument does not include a stiffening member separate from the shaft body.

10. The surgical instrument of claim 1, wherein the drive member directly contacts the inner circumferential surface of the inner cylindrical tube as the shaft body flexes.

11. The surgical instrument of claim 1, wherein each rib of the plurality of ribs has a thickness in a circumferential direction that is less than a wall thickness in a radial direction of the inner cylindrical tube.

12. A surgical instrument, comprising:
a shaft body comprising:
a proximal end and a distal end,
a length from the proximal end to the distal end,
an outer cylindrical tube,
an inner cylindrical tube positioned concentrically within and spaced from the outer cylindrical tube,
a plurality of ribs extending radially from an outer circumferential surface of the inner cylindrical tube to an inner circumferential surface of the outer cylindrical tube, and
a plurality of passages extending along the length of the shaft body from the proximal end to the distal end,
wherein the plurality of ribs connect the outer cylindrical tube and the inner cylindrical tube,
wherein each passage of the plurality of passages is defined by a first pair of opposing surfaces and a second pair of opposing surfaces,
wherein the first pair of opposing surfaces comprises surfaces of consecutively positioned ribs of the plurality of ribs,
wherein the second pair of opposing surfaces comprises the inner circumferential surface of the outer cylindrical tube and the outer circumferential surface of the inner cylindrical tube,
wherein each passage of the plurality of passages has a noncircular cross-sectional profile,
wherein each rib of the plurality of ribs has a thickness in a circumferential direction that is less than a wall thickness in a radial direction of the inner cylindrical tube, and
wherein the outer cylindrical tube, the inner cylindrical tube, and the plurality of ribs are an integral structure made from a single material;
a force transmission mechanism coupled to the proximal end of the shaft body;
a surgical end effector coupled to the distal end of the shaft body; and
a drive member operably coupled to the force transmission mechanism and the end effector, the drive member extending from the force transmission mechanism through the inner cylindrical tube to the end effector.

13. A method of manufacturing a surgical instrument, comprising:
forming a shaft body comprising:
a proximal end and a distal end,
a length from the proximal end to the distal end,
a longitudinal axis defined by the proximal and distal ends,
an outer cylindrical tube,
an inner cylindrical tube positioned concentrically within and spaced from the outer cylindrical tube,
a plurality of ribs extending radially from an outer circumferential surface of the inner cylindrical tube to an inner circumferential surface of the outer cylindrical tube, and a plurality of passages extending longitudinally along the shaft body and disposed around the longitudinal axis, wherein the plurality of ribs connect the outer cylindrical tube and the inner cylindrical tube, wherein the plurality of passages and the plurality of ribs are alternatingly disposed around the longitudinal axis of the shaft, wherein each passage of the plurality of passages is defined by a first pair of opposing surfaces and a second pair of opposing surfaces, wherein the first pair of opposing surfaces comprises surfaces of consecutively positioned ribs of the plurality of ribs, wherein the second pair of opposing surfaces comprises the inner circumferential surface of the outer cylindrical tube and the outer circumferential surface of the inner cylindrical tube, wherein each passage has a same cross-sectional area, wherein a cross-sectional area of each passage is larger than a cross-sectional area of each rib, and wherein the outer cylindrical tube, the inner cylindrical tube, and the plurality of ribs are an integral structure made from a single material;

coupling a force transmission mechanism at the proximal end of the shaft body;

coupling a surgical end effector at the distal end of the shaft body; and operatively coupling a drive member to the force transmission mechanism and the end effector, the drive member extending from the force transmission mechanism through the inner cylindrical tube to the end effector.

14. The method of claim 13, further comprising operatively coupling an electrosurgical flux transmission conduit to the end effector, the electrosurgical flux transmission conduit being positioned within a passage of the plurality of passages.

15. The method of claim 13, wherein forming the shaft body comprises extruding a single material.

16. The method of claim 13, wherein forming the shaft body comprises extruding polyether ether ketone material.

17. The method of claim 13, further comprising locating the drive member within a lumen centrally located within the inner cylindrical tube.

* * * * *